United States Patent [19]

Vanderveen et al.

[11] Patent Number: 4,608,042

[45] Date of Patent: Aug. 26, 1986

[54] APPARATUS FOR SEQUENTIAL INFUSION OF MEDICAL SOLUTIONS

[75] Inventors: Timothy W. Vanderveen, Poway; Gus Tseo, San Diego, both of Calif.

[73] Assignee: Warner-Lambert Company, Morris Plains, N.J.

[21] Appl. No.: 779,897

[22] Filed: Sep. 25, 1985

[51] Int. Cl.⁴ .................................................. A61M 5/00
[52] U.S. Cl. ..................................... 604/81; 604/135; 128/DIG. 12
[58] Field of Search ..................... 604/81, 135–139, 604/157; 128/DIG. 12, DIG.13

[56] References Cited

U.S. PATENT DOCUMENTS

| | | |
|---|---|---|
| 640,868 | 1/1900 | Bring . |
| 1,039,591 | 9/1912 | Prideaux . |
| 2,591,457 | 4/1952 | Maynes . |
| 2,866,457 | 12/1958 | Moore . |
| 2,999,499 | 12/1961 | Willet . |
| 3,276,472 | 10/1966 | Jinkens et al. .................. 137/556 |
| 3,416,567 | 12/1968 | Von Dardel et al. .............. 137/604 |
| 3,886,937 | 6/1975 | Bobo et al. . |
| 4,034,754 | 7/1977 | Virag . |
| 4,105,029 | 8/1978 | Virag . |
| 4,141,379 | 2/1979 | Manske ......................... 137/496 |
| 4,219,022 | 8/1980 | Genese . |
| 4,236,515 | 12/1980 | Genese . |
| 4,237,879 | 12/1980 | Genese . |
| 4,250,879 | 2/1981 | Muetterties . |
| 4,252,116 | 2/1981 | Genese et al. . |
| 4,256,105 | 3/1981 | Leahey et al. . |
| 4,267,836 | 5/1981 | Whitney et al. . |
| 4,298,000 | 11/1981 | Thill et al. ..................... 604/135 |
| 4,335,717 | 6/1982 | Bujan et al. . |
| 4,351,335 | 9/1982 | Whitney et al. . |
| 4,354,492 | 10/1982 | McPhee . |
| 4,381,006 | 4/1983 | Genese ..................... 128/DIG. 12 |
| 4,391,598 | 7/1983 | Thompson ...................... 604/65 |
| 4,405,316 | 9/1983 | Mittleman ...................... 604/86 |
| 4,519,792 | 5/1985 | Dawe ........................ 128/DIG. 12 |

Primary Examiner—Stephen C. Pellegrino
Attorney, Agent, or Firm—Neil K. Nydegger

[57] ABSTRACT

A system for the sequential infusion of medical solutions comprises a fluid source connected in fluid communication to a fluid flow device and having in the fluid line downstream from the fluid source a one-way check valve and a fluid access port. A spring activated syringe is connected into fluid communication with the access port to raise hydrostatic pressure downstream from the one-way check valve to prevent fluid flow therethrough during infusion by the fluid flow device of fluid from the syringe.

9 Claims, 9 Drawing Figures

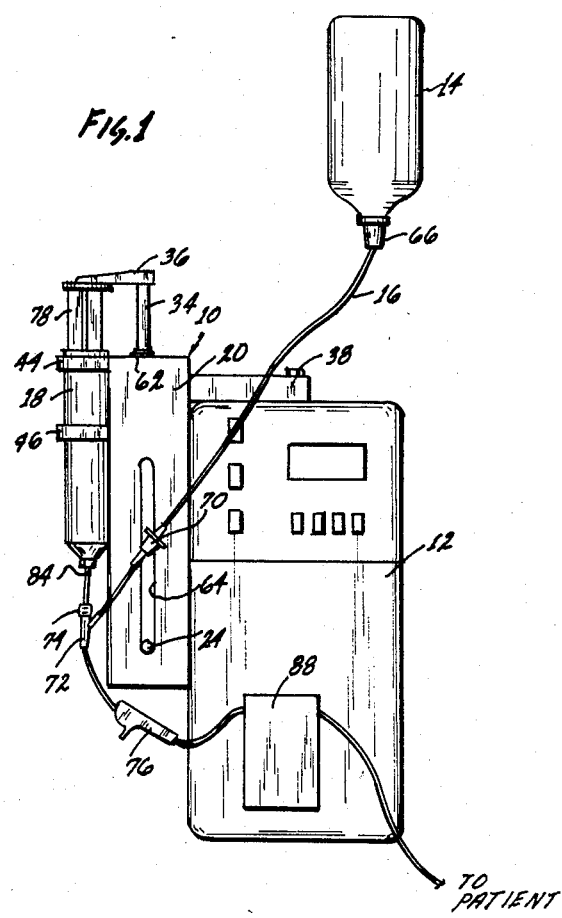
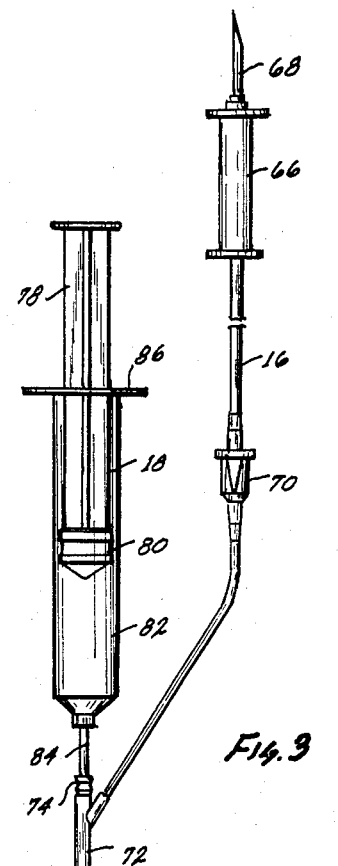
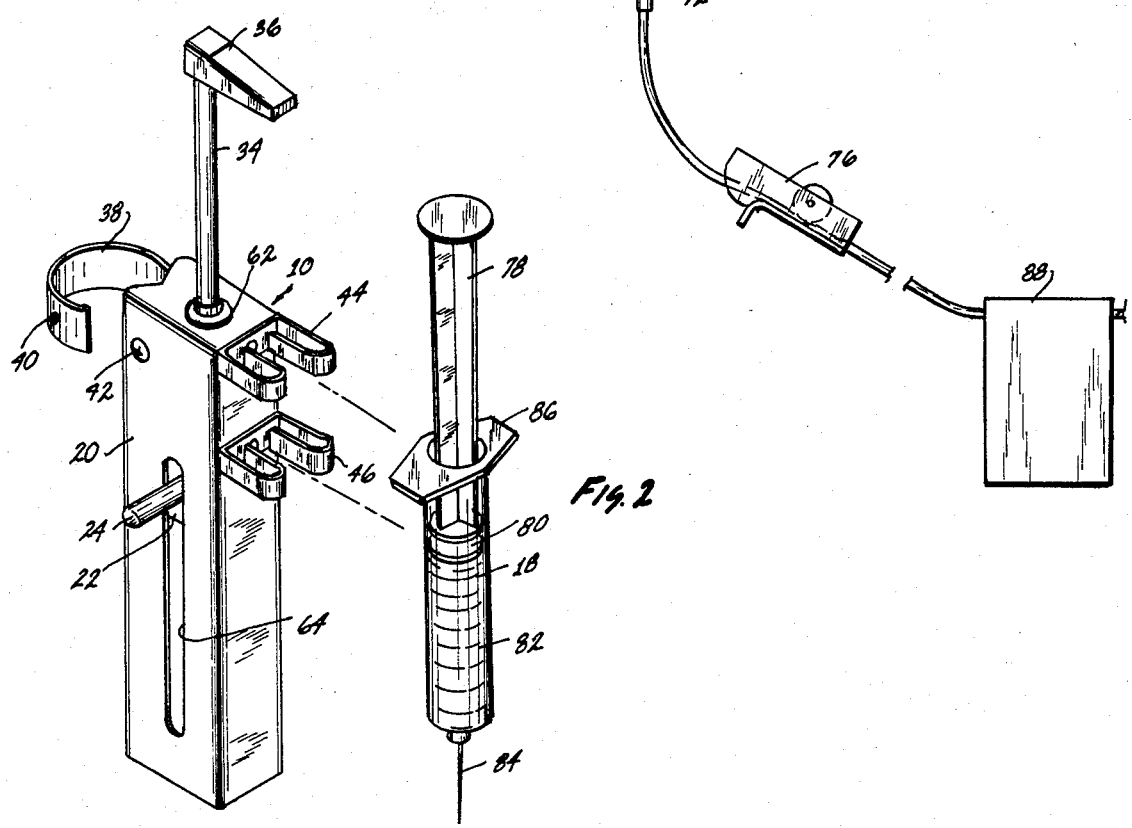
Fig. 1
Fig. 2
Fig. 3

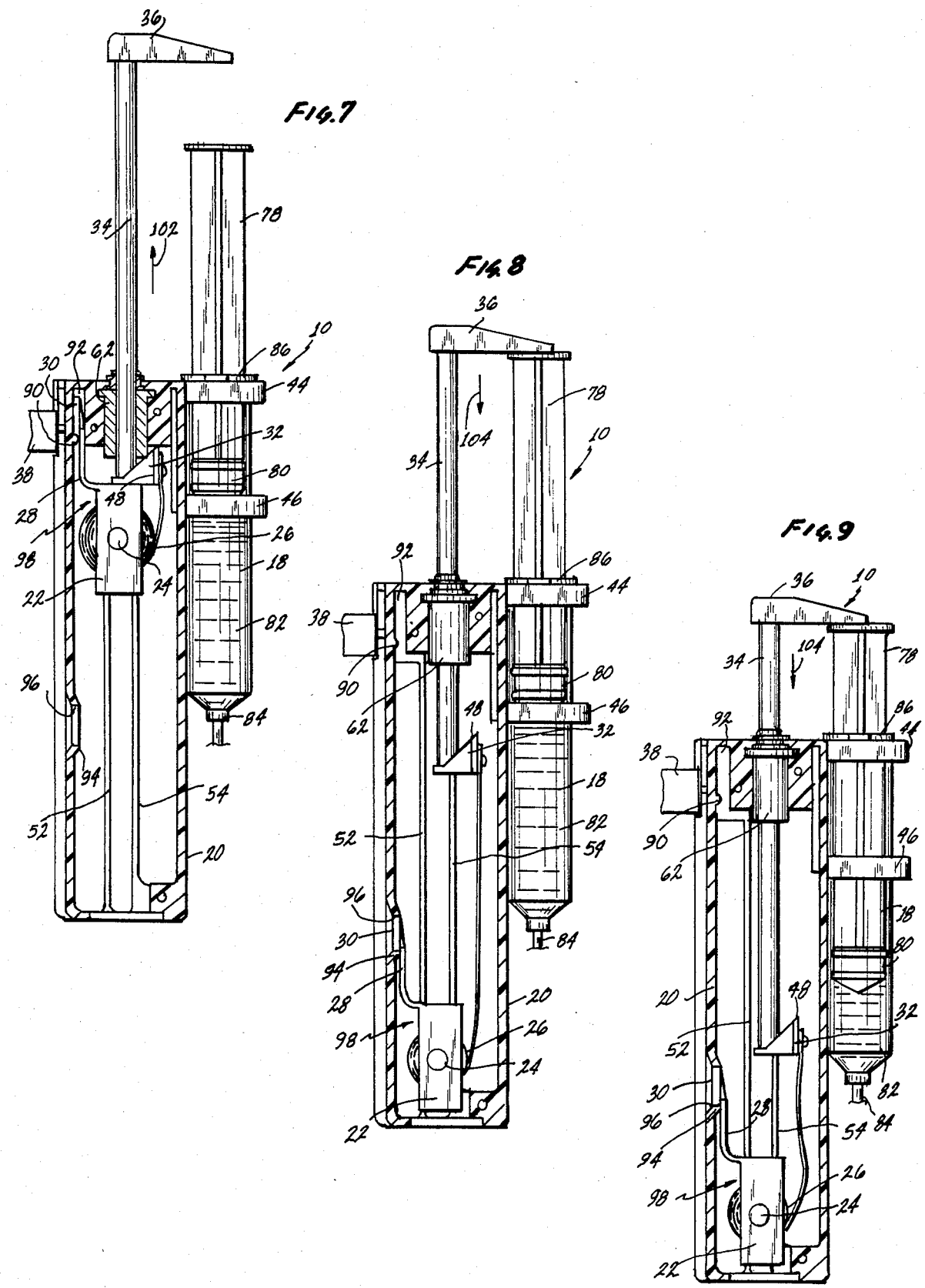

APPARATUS FOR SEQUENTIAL INFUSION OF MEDICAL SOLUTIONS

BACKGROUND OF THE INVENTION

This invention relates generally to a system for the sequential infusion of medical solutions. More particularly, the present invention relates to a piggyback infusion system wherein the secondary fluid source comprises a syringe. This invention is particularly, though not exclusively, useful for the administration of I.V. fluid to a patient from a pre-filled syringe when the patient is receiving an additional I.V. medical solution from a primary fluid source.

DESCRIPTION OF THE PRIOR ART

Hypodermic syringes are well known and have long been used for administering medical fluids or drugs to a patient. Syringes are not only relatively inexpensive and easy to use, they also provide an accurate means by which a precise quantity of fluid medicament can be established prior to its administration to a patient. For these reasons, syringes are used whenever possible in a wide variety of medical situations.

In recent years, the development of medical devices, such as pumps and controllers, has expanded the scope of infusion therapy. These devices have become widely used and are particularly effective for use when relatively large quantities of a medical fluid need to be administered to a patient over an extended period of time. In such situations, however, there is frequently still a need to administer an additional medication. Often, such additional medication is required in an amount that could be precisely and easily measured by a syringe. Thus, there is a need for an apparatus which permits effective association of a pre-filled syringe with a pump or a controller in an I.V. administration system.

Several arrangements have been established which integrate a syringe into a pump or controller activated I.V. administration system. These systems are commonly referred to as the "syringe applications." Briefly described, one such system involves the direct attachment of a syringe to the pumping chamber of a pump or to the flow constriction of a controller. A variation of the direct attachment type system includes an extension set which allows the syringe to be distanced from the fluid flow device. Still another "syringe application" involves a stop cock which is connected between the syringe and fluid flow device to permit alternate fluid flow from either the primary fluid source or the syringe by manipulation of the stop cock. Such a system is disclosed in U.S. Pat. No. 3,276,472 which issued to Jinkens et al.

Other aspects of the relevant art also needs to be mentioned. Firstly, the activation of a syringe by a spring loading device is well known. U.S. Pat. No. 1,039,591 to Prideaux discloses such a spring-assisted syringe. Also well known in the relevant art is an apparatus for administering parenteral fluids that employs a supplementary line to which a syringe may be attached. Such an apparatus is disclosed in U.S. Pat. No. 2,866,457 which issued to Moore. U.S. Pat. No. 4,237,871 to Genese is representative of the so-called piggyback systems which provide for the sequential administration of medical fluids. A refinement which provides an example of a piggyback system in which a controller is used as the fluid flow control device is disclosed and claimed in U.S. Pat. No. 4,533,347 which issued to Deckert and is assigned to the same assignee as the present invention.

Although a spring-assisted syringe is well known in the art and various piggyback type systems are well known which provide for the sequential administration of I.V. fluids to a patient, there has been no suggestion that these elements be combined. More specifically, there has been no suggestion that a spring-assisted syringe be associated with a piggyback I.V. system as the secondary fluid source to take advantage of the elevated hydrostatic pressure established in the spring-assisted syringe for sequentially establishing flow within the system. The present invention recognizes that several advantages can be obtained from such a combination. For example, unlike the secondary fluid source in a normally constituted piggyback system, the pressurized syringe need not be physically elevated above the primary fluid source in order for the piggyback system to work. Also, the system envisioned by the present invention allows the pressurized syringe, to be completely emptied without causing an occlusion alarm. In the so-called syringe application, an occlusion occurs whenever less fluid is remaining in the syringe than is capable of being handled by the pumping chamber of the fluid flow device. This problem is overcome by the present invention because, as soon as fluid has been depleted from the syringe, the fluid flow device immediately begins to infuse fluid from the primary fluid source. Thus, there is no break in the operation of the system. Still another advantage of the present invention is that by use of a syringe, it is possible to deliver a precise quantity of fluid or drug over an extended period of time without constant monitoring by the operator.

In light of the above, it is an object of the present invention to provide a mechanism by which a pre-filled syringe can be effectively integrated into a piggyback system for the sequential administration of medical solutions to a patient. It is another object of the present invention to provide a means for ensuring that all the contents of a pre-filled syringe are dispensed without causing an occlusion alarm in an I.V. administration that incorporates a volumetric infusion pump. It is yet another object of the present invention to provide an easy to use syringe activation device which facilitates the infusion of multiple medicaments to the patient.

SUMMARY OF THE INVENTION

A preferred embodiment of the present invention includes a primary fluid source and an administration set connecting the fluid source in fluid communication with a fluid flow device such as a volumetric infusion pump or an I.V. controller. Further, in sequence downstream from the primary fluid source, the administration set comprises a one-way check valve and a fluid access port. A syringe activation device is engaged with a standard hypodermic syringe to place the contents of the syringe under pressure for dispensing fluid therefrom. The activated syringe is engaged in fluid communication with the administration set via the access port to raise the hydrostatic pressure in the administration line downstream from the one-way check valve and prevent fluid flow through the one-way check valve during the dispensing of fluid from the syringe. Under these conditions, the fluid flow device acting on the fluid line will infuse fluid from the syringe to the patient. Upon depletion of fluid in the syringe, the syringe activation device ceases to exert pressure on the fluid in the administration set. This allows fluid to flow from the primary source through the one-way check valve and cause the fluid flow device to resume the infusion of fluids contained in the primary container.

As contemplated by the present invention, the fluid flow device may be either a pump or a controller. It may, however, be any other device designed for controlling the rate of fluid flow. Preferably, for purposes of the present invention, the fluid flow device is a volumetric infusion pump of the type disclosed and claimed in U.S. Pat. No. 3,985,133 which is assigned of record to the same assignee as the present invention.

The novel features of the invention, as well as the invention itself, will be best understood from the accompanying drawings taken together with the accompanying description in which similar reference characters refer to similar parts and in which:

BRIEF DESCRIPTION OF THE DRAWINGS

FIG. 1 is a front view of an I.V. infusion system showing a syringe activation device engaged with a syringe which is engaged in fluid communication with a primary administration set;

FIG. 2 is an exploded perspective view of a pre-filled syringe and the syringe activation device;

FIG. 3 is a schematic view of a fluid administration set shown in fluid communication with a pre-filled syringe;

FIG. 7 is a cross-sectional view of the syringe activation device as seen along the line 7—7 in FIG. 4 with the drive assembly in the load position;

FIG. 8 is a cross-sectional view of the syringe activation device as seen in FIG. 7 with the drive assembly in the engage position; and FIG. 9 is a cross-sectional view of the syringe activation device with the drive assembly in an operative position.

DESCRIPTION OF THE PREFERRED EMBODIMENTS

The general environment of the present invention is shown in FIG. 1 wherein a fluid flow device 12 which is capable of controlling the rate of fluid flow through the system is shown in fluid communication with both a fluid source 14 and with a fluid filled syringe 18. More specifically, a syringe activation device generally designated is shown in FIG. 1 as it cooperates with the syringe 18 and fluid flow device 12.

Figure 6:
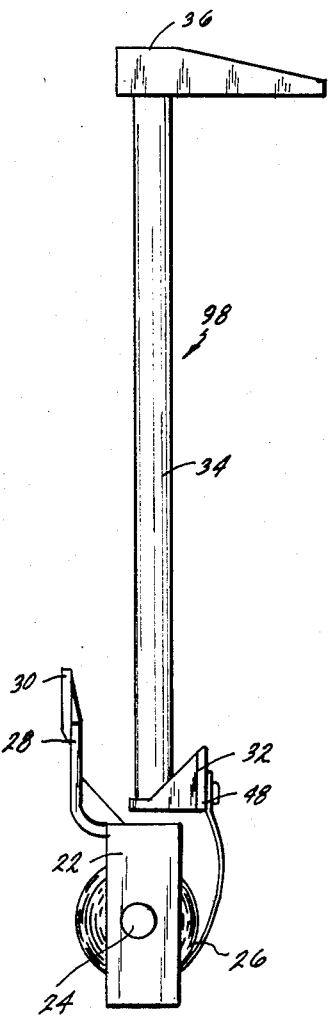
FIG. 6 is a schematic view of the drive assembly of the syringe activation device.

As best seen in FIG. 2, the syringe activation device 10 comprises a case 20. Slidably mounted within case 20 is a drive assembly generally designated 98 in FIG. 6. Referring for the moment to FIG. 6, it is seen that the drive assembly 98 includes a shuttle 22. Attached to the shuttle 22, by any means well known in the art, is a loading handle 24. Also mounted on the shuttle 24 is drive spring or negator spring 26 which is shown in FIG. 6 in the unloaded or relaxed position. As will be appreciated by the skilled artisan, an extended negator spring 26 will provide a substantially constant tension force on the objects with which it is associated. Such a spring is preferred. However, it is understod that any other spring or tension device which applies a substantially constant force over the operating range of the present invention will suffice for the purposes of the present invention. Attached at the opposite end to the negator spring 26 is a connector 32. Attached to connector 32, by any means well known in the art, is a drive shaft 34. Affixed to drive shaft 34, by any means known in the pertinent art, at the end opposite from connector 32 is a depressor 36. Also shown extending from the shuttle 22 is an arm 28 having a button 30 at the end thereof. It will be understood that arm 28 may either be attached to shuttle 22 or be formed as an integral part of the shuttle 22.

Referring back to FIG. 2, it is to be appreciated that the entire drive assembly 98 is mounted inside case 20 in a manner which will become subsequently more apparent. On the outside of case 20, a pair of mounting retainer clips 44 and 46 are attached to the case 20 and extend therefrom in a manner to be engageable with a syringe 18. Case 20 is also provided with a strap 38 having a hole 40 at one end thereof for engagement with the knob 42 in a manner that permits attachment of syringe activation device 10 with fluid flow device 12 in a manner as shown in FIG. 1.

Figure 4:
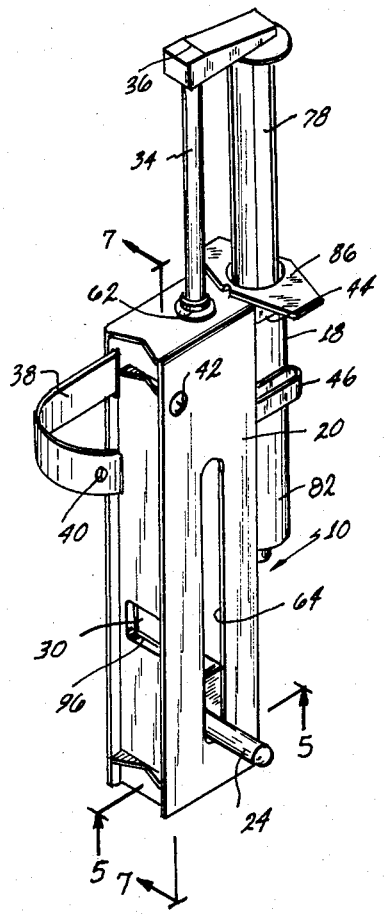
FIG. 4 is a perspective view of a pre-filled syringe engaged with a syringe activation device in the loaded configuration.
Figure 5:
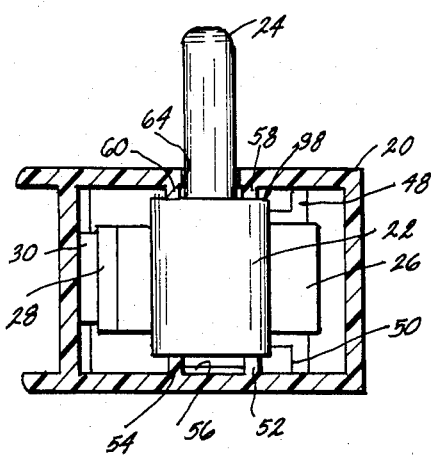
FIG. 5 is a cross-sectional view of the syringe activation device as seen along the line 5—5 in FIG. 4.

By referring to FIG. 5, the cooperation of structure between drive assembly 98 and case 20 will be more readily appreciated. As seen in FIG. 5, a portion of shuttle 22 rests within groove 56 which is formed by the rails 52 and 54. A cross-referrence at this point with FIG. 7 shows that the shuttle 22 is confined in case 20 to slide along the groove 56 between rails 52 and 54. As best seen in FIG. 5, the connector 32 is formed with extenders 48 and 50 which are of sufficient length to come into sliding contact with the interior of case 20 and help provide stability for both drive shaft 34 and shuttle 22. Also seen in FIG. 5 and formed on the case 20 are flanges 58 and 60 which slidably urge against the shuttle 22 to help provide additional stability for shuttle 22 as it moves reciprocally along groove 56 of case 20. The mounting of drive assembly 98 within case 20 is further illustrated in FIG. 7 where it is seen that the drive shaft 34 is slidably disposed within bushing 62. Further, as clearly seen in FIGS. 2, 4 and 5, the drive assembly 98 is positioned in case 20 in a manner that permits loading handle 24 to extend through slot 64 and permit movement of the shuttle 22 within case 20 by manipulation of the loading handle 24.

The mounting of syringe 18 on syringe activation device is best appreciated by cross-referencing FIGS. 2, 4 and 7. In FIG. 2 the basic components of a pre-filled syringe are shown as being the syringe 18 and a plunger 80 which is directly connected to plunger handle 78. Plunger 80 is slidably mounted within fluid chamber 82 of syringe 18 in a manner which permits its movement to expel fluid from syringe 18 through needle 84. In its engagement with the syringe activation device 10, it can be seen in FIGS. 4, 7, 8 and 9 that syringe 18 is placed in clipping engagement with retainer clips 44 and 46 in a manner that causes the finger grips 86 of syringe 18 to rest against retainer clip 44. Further, as envisioned by the present invention, the depressor 36 would urge against the plunger handle 78 in a manner as shown in FIG. 4 so that the movement of depressor 36 will urge plunger handle 78, and consequently plunger 80, into the fluid chamber 82 to expel fluid from the syringe 18.

The primary fluid line of the system is shown in FIG. 3 and includes a drip chamber 66 having a spike 68 which is engageable in a manner well known in the pertinent art to a fluid source 14 as shown in FIG. 1. As further shown in FIG. 3, the fluid line downstream from drip chamber 66 includes integral with the tubing set 16 a one-way check valve 70 which may be of any type well known in the pertinent art. In the preferred embodiment, one-way check valve 70 is of the duck-bill type. Further downstream from fluid source 14 in the primary tubing set 16 is a fluid access port 74. As will be appreciated by the skilled artisan, fluid access port 74 can be part of a standard Y-site connector 72. Further downstream in tubing set 16 is a clamping device 76 which may be of any type well known in the art. As shown in FIG. 3, the clamping device 76 is a standard roller type clamp. Tubing set 16 then extends from the Y-site 72 to the pumping chamber 88 of fluid flow device 12. It should be appreciated by the skilled artisan and more clearly appreciated subsequently that the fluid flow device 12 may be any type of device that is capable of controlling fluid flow rate. It will be understood that the fluid flow device 12 can be a pump, a controller or even a clamping device. It is important for the purposes of the present invention that the fluid flow device 12 be capable of sustaining fluid pressure and providing the type of constriction or restriction that allows for an increase in fluid pressure upstream from the pump chamber 88.

Referring again to FIG. 7, it can be seen that case 20 is formed with a detent 90 which defines a detent recess 92. Additionally, and for purposes to become subsequently clearer, case 20 is formed with a lip 94 that defines an opening 96. It is important that opening 96 be of sufficient size to capture button 30 and hold button 30 therein by the action of lip 94 when the button 30 is aligned with the opening 96.

OPERATION

In its operation the syringe activation device 10 is used to pressurize a syringe 18 and consequently deliver I.V. solution to fluid flow device 12 at elevated hydrostatic pressure. Typically, a primary fluid flow line is established by connecting fluid source 14 into fluid communication with fluid flow device 12 by means of a tubing set 16. In the present invention the tubing set 16 comprises in sequence downstream from the fluid source 14 a one-way check valve 70 and a Y-site 72 having a fluid access port 74 integral therewith. For purposes to become subsequently clearer, the fluid access port 74 is capable of achieving fluid communication with a syringe 18.

As envisioned in the present invention, the drive assembly 98 of syringe activation device 10 will be positioned in an engaging position as shown in FIG. 7 when drive assembly 98 is moved in the direction of arrow 102 and the button 30 on shuttle 22 is positioned within the detent recess 92 and held there by detent 90. In this position the extendable negator spring 26 has not been extended and therefore there is no force acting on depressor 36 through drive shaft 34 to urge depressor 36 toward the shuttle 22. As seen in FIG. 7, syringe 18 is engageable with syringe activation device 10 by placing syringe 18 in retainer clips 44 and 46 with finger grip 86 of the syringe 18 resting against retainer clip 44. Further engagement of syringe activation device 10 with syringe 18 is accomplished by grasping loading handle 24 to move the shuttle 22 in the direction of arrow 104 to disengage button 30 from detent recess 92. This also places depressor 36 into contact with plunger handle 78.

Syringe activation device 10 is activated by forcing loading handle 24 to position shuttle 22 as shown in FIGS. 8 and 9. In this position button 30 is held within opening 96 by lip 94. A cross-reference with FIG. 4 will show that with the device 10 activated as shown in FIG. 9, the operator has access to button 30 through opening 96 in a manner which will permit depression of the button 30 to release shuttle 22 from its position, if a release is desired by the operator. FIGS. 8 and 9 also show that the extendable negator spring 26 has been extended such that a force is now placed upon drive shaft 34 which urges depressor 36 against plunger handle 78 in a manner that tends to advance plunger 80 into fluid chamber 82 of syringe 18 for dispensing fluid from syringe 18 as indicated by comparing FIG. 8 with FIG. 9.

From the above discussion, it will be appreciated by the skilled artisan that activation of the device 10 is accomplished by manipulation of the drive assembly 98 in the sequence as shown in FIGS. 7, 8 and 9, respectively. With the syringe 18 loaded as shown in FIG. 8, the syringe 18 is placed into fluid communication with tubing set 16 with the penetration of fluid access port 74 by needle 84 of syringe 18. In this combination the action of device 10 on syringe 18 will raise hydrostatic pressure in the fluid line downstream from the one-way check valve 70. Fluid at a lower hydrostatic pressure in the fluid source 14 is thereby prevented from flowing through the one-way check valve 70 toward fluid flow device 12. Accordingly, any action of fluid flow device 12 will be on the fluid contained in the system downstream from one-way check valve 70. The result is that fluid contained within syringe 18 is used by fluid flow device 12 for infusion to the patient so long as syringe activation device 10 is acting upon syringe 18 to elevate the hydrostatic pressure in the system downstream from the one-way check valve 70. Once all fluid is dispensed from syringe 18, the movement of plunger 80 within the syringe 18 will be stopped. At this point the action of device 10 on syringe 18 will have ceased and the elevation of hydrostatic pressure in the system downstream from one-way check valve 70 will no longer be elevated above the hydrostatic pressure of fluid upstream from the one-way check valve 70. Under this condition the one-way check valve 70 will no longer prevent fluid flow and fluid flow device 12 will begin act on fluid coming from fluid source 14.

Once the fluid from syringe 18 has been dispensed and the system has resumed infusion of fluids to the patient from fluid source 14, the syringe 18 and its associated syringe activation device 10 can be removed from the system. It will be appreciated that at this time another pre-filled syringe and associated syringe activation device can be introduced into the system. It should also be appreciated that prior to the completion of dispensing fluids from the syringe 18, device 10 can be removed from the pump and button 30 depressed to stop the action of drive assembly 98 on the plunger handle 78. Once button 30 has been depressed, syringe 18 can be disengaged from fluid access port 74.

While the particular syringe activation device 10 and the system for sequential infusion of medical solutions to a patient as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

We claim:

1. An apparatus for the sequential infusion of I.V. fluids to a patient comprising:
   a fluid source;
   a fluid flow device;
   an I.V. tubing set connecting said fluid source in fluid communication with said fluid flow device, said tubing set comprising in sequence, downstream from said fluid source, a one-way check valve and a fluid access port;
   means on said fluid flow device to control the rate of fluid flow therethrough;
   a pre-filled syringe, having a fluid chamber and a Plunger slidably positioned therein, connectable in fluid communication with said access port; and
   an activation means comprising: a case; a shuttle slidably mounted on said case for movement between a first position and a second position; a drive shaft having a depressor affixed thereto; a normally relaxed spring connecting said drive shaft to said shuttle; clips attached to said case for mounting said syringe on said case to position said depressor against said plunger and establish said shuttle in the first position; and a handle fixedly mounted on said shuttle for moving said shuttle from the first position into the second position to extend said spring for urging said depressor against said plunger to dispense fluid from said chamber of said syringe and sufficiently raise the hydrostatic pressure downstream from said one-way check valve to prevent fluid flow therethrough when said syringe is engaged with said access port for the infusion of fluid from said syringe by said fluid flow device to the patient.

2. An apparatus as cited in claim 1 wherein said spring is a negator spring.

3. An apparatus as cited in claim 1 wherein said fluid flow device is a pump.

4. An apparatus as cited in claim 1 wherein said fluid flow device is a controller.

5. An apparatus as cited in claim 1 further comprises a clamping device operatively engageable with said tubing set downstream from said access port to prevent fluid flow therethrough.

6. A syringe activation device, for use with a volumetric infusion pump to sequentially dispense I.V. fluids to a patient from a pre-filled syringe having a plunger handle and from a fluid source, which comprises:
   a case;
   a shuttle;
   a drive shaft having a depressor affixed thereto;
   a spring means connecting said drive shaft to said shuttle;
   means for mounting said pre-filled syringe on said case;
   means for slidably mounting said shuttle on said case for reciprocal movement between a first position wherein said spring means is relaxed and said depressor is positioned against said plunger handle, and a second position wherein said spring means is extended to urge said depressor against said plunger handle for dispensing fluid from said syringe;
   means for locking said shuttle in said second position;
   means for connecting said syringe in fluid communication with said pump; and
   means for preventing fluid flow from said fluid source when said syringe is dispensing fluid to said pump.

7. A syringe activation device as recited in claim 6 wherein said spring means is a negator spring.

8. A syringe activation device as recited in claim 7 wherein said fluid flow prevention means is a one-way check valve.

9. A method for sequentially administering medical fluids from a syringe with a plunger and from a fluid source which comprises the steps of:
   a. engaging said syringe with a syringe activation device which comprises: a case; a shuttle slidably mounted on said case for movement btween a first position and a second position; a drive shaft having a depressor affixed thereto; a normally relaxed spring connecting said drive shaft to said shuttle; clips attached to said case for mounting said syringe thereon to position said depressor against said plunger and establish said shuttle in the first position; and a handle fixedly mounted on said shuttle for moving said shuttle from the first position into the second position to extend said spring for urging said depressor against said plunger to dispense fluid from said chamber of said syringe;
   b. establishing an I.V. administration system comprising: a fluid source; a fluid flow device; an I.V. tubing set connecting said fluid source in fluid communication with said fluid flow device for infusing fluid from said fluid source to the patient, said tubing set comprising in sequence, downstream from said fluid source, a one-way check valve and a fluid access port; means on said fluid flow device to control the rate of fluid flow therethrough; and
   c. connecting said combination of said syringe and said syringe activation device in fluid communication with said I.V. administration system at said access port to sufficiently raise the hydrostatic pressure downstream from said one-way check valve to prevent fluid flow therethrough when said syringe is engaged with said access port for the infusion of fluid from said syringe by said fluid flow device to the patient.

* * * * *